United States Patent [19]
Lewis et al.

[11] Patent Number: 5,552,302
[45] Date of Patent: Sep. 3, 1996

[54] METHODS AND COMPOSITIONS FOR PRODUCTION OF HUMAN RECOMBINANT PLACENTAL RIBONUCLEASE INHIBITOR

[75] Inventors: Martin K. Lewis, Madison; John W. Shultz, Verona, both of Wis.

[73] Assignee: Promega Corporation, Madison, Wis.

[21] Appl. No.: 282,151

[22] Filed: Jul. 27, 1994

Related U.S. Application Data

[63] Continuation of Ser. No. 856,863, Mar. 24, 1992, abandoned, which is a continuation of Ser. No. 510,881, Apr. 18, 1990, abandoned, which is a continuation-in-part of Ser. No. 342,362, Apr. 24, 1989, abandoned.

[51] Int. Cl.⁶ .............................. C07K 1/14; C07K 1/30; C12P 21/02
[52] U.S. Cl. ........................ 435/692; 530/412; 530/418
[58] Field of Search ....................... 435/69.2; 530/412, 530/415, 418

[56] References Cited

U.S. PATENT DOCUMENTS

| | | | |
|---|---|---|---|
| 4,673,641 | 6/1987 | George et al. | 435/69.1 |
| 4,734,362 | 3/1988 | Hung et al. | 435/68.1 |
| 4,923,967 | 5/1990 | Bobbitt et al. | 530/351 |
| 4,966,964 | 10/1990 | Shapiro et al. | 536/23.2 |
| 5,019,556 | 5/1991 | Shapiro et al. | 514/2 |
| 5,082,775 | 1/1992 | McCaman et al. | 435/69.7 |
| 5,220,013 | 6/1993 | Ponte et al. | 536/23.5 |

FOREIGN PATENT DOCUMENTS 0291686  11/1988  European Pat. Off. .

OTHER PUBLICATIONS

Marston et al., Meth. Enzymol. 182:264–276 (1990).
Saitoh et al., J. Biochem. 101:1281–1288 (1987).
Crawford et al., Gene 85:525–531 (1989).
Marston et al., Biochem. J. 240:1–12 (1986).
Kane et al., Trends Biotechnol. 6:95–101 (1988).
Maniatis et al., *Molecular Cloning: A Laboratory Manual*, Cold Spring Harbor Laboratory, Cold Spring Harbor, NY, 1982, pp. 89–92.
Marston, "The Purification of Eukaryotic Polypeptides Expresses in Eschericia coli," in *DNA Cloning: A Practical Approach*, D. M Glover, ed., IRL Press, Oxford, England, vol. III, Chap. 4, pp. 59–88 (1987).
Lee et al. "Correction," Biochemistry 28, 7138 (1989).
Lee, et al., *Biochemistry*, 1989, vol. 28, pp. 225–230, ibid pp. 219–224.
Lee, F. S. and Valle, B. L., *Biochemical and Biophysical Research Communications*, 1989, vol. 160(1), pp. 115–120.
Young, Richard A. and Ronald W. Davis, "Efficient Isolation of Genes by Using Antibody Probes," *Proc. Natl. Acad. Sci. U.S.A.*, 80:1194–1198 (1983).
Hoess, Adolf, et al., "Recovery of Soluble, Biologically Active Recombinant Proteins from Total Bacterial Lysates Using Ion Exchange Resin," *Biotechnology*, 6:1214–1217 (1988).

Blackburn, Peter, et al., "Ribonuclease Inhibitor from Human Placenta," *The Journal of Biological Chemistry*, 252/16:5904–5910 (1977).
Shapiro, Robert and Bert L. Vallee, "Human Placental Ribonuclease Inhibitor Abolishes both Angiogenic and Ribonucleolytic Activities of Angiogenin, " *Proc. Natl. Acad. Sci. U.S.A.*, 84:2238–2241 (1987).
Townbin, Harry, et al., "Electrophoretic Transfer of Proteins from Polyacrylamide Gels to Nitrocellulose Sheets: Procedure and Some Applications," *Proc. Natl. Acad. Sci. U.S.A.*, 76/9:4350–4354 (1979).
Rosenberg, Alan H., et al., "VEctors for Selective Expression of Cloned DNAs by T7 RNA Polymerase," *Gene*, 56:125–135 (1987).
Studier, F. William and Barbara A. Moffatt, "Use of Bacteriophage T7 RNA Polymerase to Direct Selective High–level Expression of Cloned Genes," *J. Mol. Biol.*, 189:113–130 (1986).
Laemmli, U. K., "Cleavage of Structural Proteins During the Assembly of the Head of Bacteriophage T4," *Nature*, 227:680–685 (1970).
Stark, Michael J. R., "Multicopy Expression Vectors Carrying the lac Repressor Gene for Regulated High–Level Expression of Genes in *Escherichia coli*," *Gene*, 51:255–267 (1987).
Inouye, Massayori, "Experimental Manipulation of Gene Expression," Ed., Academic Press, pp. 15–32 (1983).
Movva, N. Rao, et al., "Gene Sructure of the OmpA Protein, a Major Surface Protein of *Escherichia coli* Required for Cell–Cell Interaction," *J. Mol. Biol., 143:329–334 (1980)*.
Blackburn, Peter, "Ribonuclease Inhibitor from Human Placenta: Rapid Purification and Assay," The Journal of Biological Chemistry, 254/24:12484–12487 (1979).
Blackburn, Peter and Stanford Moore, "The Enzymes, vol. XV, Nucleic Acids, Part B," Ed., Academic Press, pp. 416–424 (1982).
Lee, Frank S., et al., "Primary Structure of Human Placental Ribonuclease Inhibitor," *Biochemistry*, 27:8545–8553 (1988).
Schneider, Rainer, et al., "The Primary Structure of Human Ribonuclease/ Angiogenin Inhibitor (RAI) Discloses a Novel Highly Dviersified Protein Super–family with a Common Repetitive Module," *EMBO Journal*, 7/13:4151–4156 (1988).

(List continued on next page.)

Primary Examiner—Robert A. Wax
Assistant Examiner—Eric Grimes
Attorney, Agent, or Firm—Foley & Lardner

[57] ABSTRACT

The in vitro cloning of a gene for human placental ribonuclease inhibitor may be obtained by recombinant DNA technology. The method described obtains the gene encoding human placental ribonuclease inhibitor, the expression of that product in a host cell, and the refolding and purifying of the product. A vector which includes an encoded DNA gene sequence coding for human placental ribonuclease inhibitor is also described, as well as a host that is compatible with and contains the vector. The gene sequence of the human placental ribonuclease inhibitor is also presented.

13 Claims, 7 Drawing Sheets

OTHER PUBLICATIONS

Erase–a–Base™ System Technical Manual (Promega) (1987).

ProtoBlot® Western Blot AP System TEchnical Manual (Promega) (1987).

ProtoBlot® Immunoscreening System Technical Manual (Promega) (1987).

Riboprobe® Gemini System: pGEM–5Zf(+) and pGEM–7Zf(+) Vectors Product Description (Promega) (1988).

LambdaSorb™ Phage Adsorbent Product Description (Promega) (1988).

Erase–a–Base® System Product Description (Promega) (1985).

RNasin® Ribonuclease Inhibitor (Promega) (1988).

Nucleotide Sequence of the Cloned RNasin Insert:

GAATTCGGGTCCACC<u>ATG</u> AGC CTG GAC ATC CAG AGC CTG GAC ATC CAG
                     M   S   L   D   I   Q   S   L   D   I   Q

TGT GAG GAG CTG AGC GAC GCT AGA TGG GCC GAG CTC CTC CCT CTG
  C   E   E   L   S   D   A   R   W   A   E   L   L   P   L

CTC CAG CAG TGC CAA GTG GTC AGG CTG GAC GAC TGT GGC CTC ACG
  L   Q   Q   C   Q   V   V   R   L   D   D   C   G   L   T

GAA GCA CGG TGC AAG GAC ATC AGC TCT GCA CTT CGA GTC AAC CCT
  E   A   R   C   K   D   I   S   S   A   L   R   V   N   P

GCA CTG GCA GAG CTC AAC CTG CGC AGC AAC GAG CTG GGC GAT GTC
  A   L   A   E   L   N   L   R   S   N   E   L   G   D   V

GGC GTG CAT TGC GTG CTC CAG GGC CTG CAG ACC CCC TCC TGC AAG
  G   V   H   C   V   L   Q   G   L   Q   T   P   S   C   K

ATC CAG AAG CTG AGC CTC CAG AAC TGC TGC CTG ACG GGG GCC GGC
  I   Q   K   L   S   L   Q   N   C   C   L   T   G   A   G

TGC GGG GTC CTG TCC AGC AGA CTA CGC ACC CTG CCC ACC CTG CAG
  C   G   V   L   S   S   T   L   R   T   L   P   T   L   Q

FIG. 3

```
GAG CTG CAC CTC AGC GAC AAC CTC TTG GGG GAT GCG GGC CTG CAG
 E   L   H   L   S   D   N   L   L   G   D   A   G   L   Q

CTG CTC TGC GAA GGA CTC CTG GAC CCC CAG TGC CGC CTG GAA AAG
 L   L   C   E   G   L   L   D   P   Q   C   R   L   E   K

CTG CAG CTG GAG TAT TGC AGC CTC TCG GCT GCC AGC TGC GAG CCC
 L   Q   L   E   Y   C   S   L   S   A   A   S   C   E   P

CTG GCC TCC GTG CTC AGC GCC AAG CCC GAC TTC AAG GAG CTC ACG
 L   A   S   V   L   S   A   K   P   D   F   K   E   L   T

GTT AGC AAC AAC GAC ATC AAT GAG GCT GGC GTC CGT GTG CTG TGC
 V   S   N   N   D   I   N   E   A   G   V   R   V   L   C

CAG GGC CTG AAG GAC TCC CCC TGC CAG CTG GAG GCG CTC AAG CTG
 Q   G   L   K   D   S   P   C   Q   L   E   A   L   K   L

GAG AGC TGC GGT GTG ACA TCA GAC AAC TGC CGG GAC CTG TGC GGC
 E   S   C   G   V   T   S   D   N   C   R   D   L   C   G

ATT GTG GCC TCC AAG GCC TCG CTG CGG GAG CTG GCC CTG GGC AGC
 I   V   A   S   K   A   S   L   R   E   L   A   L   G   S

AAC AAG CTG GGT GAT GTG GGC ATG GCG GAG CTG TGC CCA GGG CTG
 N   K   L   G   D   V   G   M   A   E   L   C   P   G   L
```

FIG. 3A

```
CTC CAC CCC AGC TCC AGG CTC AGG ACC CTG TGG ATC TGG GAG TGT
 L   H   P   S   S   R   L   R   T   L   W   I   W   E   C

GGC ATC ACT GCC AAG GGC TGC GGG GAT CTG TGC CGT GTC CTC AGG
 G   I   T   A   K   G   C   G   D   L   C   R   V   L   R

GCC AAG GAG AGC CTG AAG GAG CTC AGC CTG GCC GGC AAC GAG CTG
 A   K   E   S   L   K   E   L   S   L   A   G   N   E   L

GGG GAT GAG GGT GCC CGA CTG CTG TGT GAG ACC CTG CTG GAA CCT
 G   D   E   G   A   R   L   L   C   E   T   L   L   E   P

GGC TGC CAG CTG GAG TCG CTG TGG GTG AAG TCC TGC AGC TTC ACA
 G   C   Q   L   E   S   L   W   V   K   S   C   S   F   T

GCC GCC TGC TGC TCC CAC TTC AGC TCA GTG CTG GCC CAG AAC
 A   A   C   C   S   H   F   S   S   V   L   A   Q   N

AGG TTT CTC CTG GAG CTA CAG ATA AGC AAC AAC AGG CTG GAG GAT
 R   F   L   L   E   L   Q   I   S   N   N   R   L   E   D

GCG GGC GTG CGG GAG CTG TGC CAG GGC CTG GGC .....GGAGCAGCTGGT
 A   G   V   R   E   L   C   Q   G   L   G

CCTGTACGACATTTACTGGTCTGAGGAGATGGAGGACCGGCTGCAGGCCCTGGAGAAG
```

FIG. 3B

GACAAGCCATCCCTGAGGGTCATCTCCTGAGGCTCTTCCTGCTGCTGCTCTCCCTGGA

CGACCGGCCTCGACGCAACCCTGGGCCCACCAGCCCCTCCCATGCTCTCACCCTGCA

TATCCTAGGTTTGAAGAGAAACGCTCAGATCCGCTTATTTCTGCCAGTATATTTTGGA

CACTTTATAATCATTAAAGCACTTTCTTGGCAAAAAAAAAAAAAAAAAAAAAAAAAAA

AAAAAAAAA

FIG. 3C

METHODS AND COMPOSITIONS FOR PRODUCTION OF HUMAN RECOMBINANT PLACENTAL RIBONUCLEASE INHIBITOR

This is a continuation of application Ser. No. 856,863, filed Mar. 24, 1992, abandoned, which is a continuation of application Ser. No. 510,881, filed Apr. 18, 1990, abandoned, which is a continuation-in-part of application Ser. No. 342,362, filed Apr. 24, 1989, abandoned.

BACKGROUND OF THE INVENTION

1. Field of the Invention

The present invention relates to recombinant DNA technology. More specifically, it involves the creation of a cDNA genetic sequence encoding for human recombinant placental ribonuclease inhibitor, a vector containing this gene, and a host containing the cDNA gene.

2. Description of the Prior Art

Through the development of recombinant DNA techniques, it has become fairly straightforward to clone sequences from essentially any organism into plasmid or viral vectors for propagation and amplification in a foreign host. In this form the DNA can be studied with regard to its sequence, structure, coding capacity or other properties. It can also be used for a variety of applications such as detection of complementary sequences in samples, generation of altered forms of a gene product, modulation of organismal function through insertion into new organisms, etc.

The advent of recombinant DNA (rDNA) technology has also resulted in the isolation of coding sequences of complementary DNA (cDNA) using antibody probes. Young, R. A. and R. W. Davis, *Proc. Natl. Acad. Sci. U.S.A.*, 80, 1194–1198 (1983). This system incorporates features that maximize the ability to detect antigenic determinants (epitopes) on polypeptides expressed from the DNA of any source. Successful isolation of genomic or cDNA sequences using this system requires both a cDNA library and an antibody probe of adequate quality. Mierendorf, Robert C., et al., "Gene Isolation by Screening [Lambda] gt11 Libraries with Antibodies," *Guide to Molecular Cloning Techniques*, 152, 458–469 (1987). The application of this technology has led to the isolation of the gene coding for a particular protein to which an antibody has been raised. Even so, gene isolation using this technology is by no means assured. For example, in some cases the construct that one seeks may prove to be lethal to the host cell, most generally *E. coli*. In other cases, the isolation of the gene is made difficult by producing antibodies mainly against the carbohydrate portion of the target protein, especially when the carbohydrate is not added onto the protein when synthesized within the *E. coli* cell. In situations like this, the antibody is not useful for detection. A further complication is the appearance of weak positives on the immunoscreening filter. The weak positives presumably are proteins which are recognized by antibodies against contaminants in the immunizing protein preparation. Alternatively, the weak positives may be other proteins with shared immunogenicity to the protein of interest.

Final proof that the target protein has been cloned will depend upon achieving activity of the recombinant protein synthesized in *E. coli*. This is sometimes not possible since many eukaryotic proteins are synthesized in a misfolded, insoluble and inactive form in *E. coli*. Hoess, A., et al., "Recovery of Soluble, Biologically Active Recombinant Proteins from Total Bacterial Lysates Using Ion Exchange Resin," *Biotechnology*, 6, 1214–1217 (1988). In some cases the inactive, insoluble protein can be solubilized and refolded into an active form. However, the determination of the conditions essential for the efficient recovery of the active form of a protein requires significant experimentation to optimize many parameters that can affect the refolding process. See Marston, F.A.O., "The Purification of Eukaryotic Polypeptides Expressed in *Escherichia coli*," *DNA Cloning, Vol. III, A Practical Approach*, Chap. 4, D. M. Glover, Ed., IRL Press, 1987, and the references cited therein. Thus, the testing of a cloned gene encoding a particular protein depends on many factors that cannot be predicted before experimentation is initiated.

It is generally thought that the isolation of a cDNA clone, i.e., a double-stranded DNA which corresponds to the information present in the RNA for the protein, first involves sufficiently purifying enough of the protein of interest and developing an antibody against that protein in an appropriate animal, such as a rabbit. The next step is to use the antibody as an immunoprobe to screen a cDNA library of the tissue where such protein is expressed. cDNA libraries are most frequently constructed in bacteriophage lambda vectors, and particularly the bacteriophage vector lambda gt11 when an antibody probe is available for screening. This is because lambda gt11 is an expression vector, meaning that a fusion protein is formed between *E. coli* beta galactosidase, a natural *E. coli* enzyme, and the protein from the cDNA inserts. Jendrisak, Jerry, et al. (1987) "Cloning cDNA into [Lambda] gt10 and [Lambda] gt11," *Guide to Molecular Cloning Techniques*, 152, 359–371 (1987). The gene for the protein of interest, present in the form of a DNA copy of the RNA, is also present in the lambda gt11 under the control of an *E. coli* promoter.

When the recombinant bacteriophage encoding for the desired protein infects *E. coli* cells, some of the recombinant fusion protein is produced and released from the cells due to cell lysis in the bacteriophage plaque. This protein is picked up on a nitrocellulose filter, and the protein is detected with the antibody against the protein of interest. The screening procedure is repeated until homogeneous phage plaques carrying the foreign gene are produced. The gene is then ready for subcloning into a plasmid, a small circular form of DNA that can replicate independently of the DNA in the genome, and for engineering for expression.

This technology has been applied to human placental ribonuclease inhibitor (PRI). Blackburn, Peter, et al., "Ribonuclease Inhibitor from Human Placenta," *The Journal of Biological Chemistry*, 252/16, 5904–5910 (1977). Blackburn, et al. disclose the preparation of a soluble PRI, which had been purified 4,000 fold by a combination of ion exchange and affinity chromatography. PRI was found to be an acidic protein of molecular weight near 50,000.

Natural PRI is a protein isolated from human placenta which specifically inhibits ribonucleases (RNases), an enzyme that catalyzes the breakdown of RNA. It functions by binding tightly to a wide spectrum of RNases and can be very useful wherever strong RNase inhibition may be essential to protect RNA. PRI is a protein of interest, having great promise for utility in research and other purposes. Although the physiological role of the protein has not yet been established, recent data have suggested that the in vivo role of the protein may be the regulation of blood vessel development. Shapiro, Robert and Bert L. Vallee, "Human Placental Ribonuclease Inhibitor Abolishes Both Angiogenic and Ribonucleolytic Activities of Angiogenin," *Proc. Natl. Acad. Sci. USA*, 84, 2238–2241 (1987). Shapiro and vallee established the relationship between PRI and angiogenin.

The results of their experiments suggest that PRI and related inhibitors may participate in the in vivo regulation of angiogenin, a blood vessel-inducing protein from HT-29 human:adeno-carcinoma cells. Human PRI has been found to abolish both the biological and enzymatic activities of angiogenin, thus further confirming that the angiogenin/PRI interaction is functionally significant. Because of the possible participation of angiogenin in creating states of pathological vascularization such as occur in a variety of diseases including tumor metastasis, diabetic retinopathy and rheumatoid arthritis, the tight interaction with and inhibition of angiogenin by PRI could potentially be a useful therapeutic route to treat these diseases. Thus, PRI may have important mechanistic, physiologic, pharmacologic and/or therapeutic implications. Still other functions for this protein are likely to be discovered.

To study the role of the protein PRI in animals requires a pure source which is free from the impurities that may be present in preparations from the human placental source. These impurities are mammalian proteins, possibly prions, and mammalian DNA, some of which may be from viral sources such as HIV and hepatitis virus. Unfortunately, it is relatively expensive to extract a sufficient amount of tile purified protein from natural sources. Thus, there is a need for a source of large, less expensive quantities of human PRI which are essentially free of impurities.

SUMMARY OF THE INVENTION

In accordance with the present invention, it is now possible to obtain usable quantities of a cloned, active gene product of human PRI which is free from contaminants. The procedure involves the steps of isolating the natural gene encoding for human PRI starting with a sample of human PRI, screening a DNA library for the presence of a cloned gene, forming a human PRI plasmid construct, introducing the plasmid construct into a host cell, and isolating the human PRI protein by cell lysis followed by centifugation to recover the human PRI.

The present invention is also directed to a method of purifying, solubilizing, and refolding isolated PRI, which includes centrifuging the crude PRI obtained by the method described above to purify the human PRI, solubilizing the human PRI with a chemical agent, and combining a sufficient amount of buffer with the solubilized PRI to allow the human PRI to refold.

The present invention also encompasses a vector comprising an inserted DNA gene sequence coding for human PRI, a host that is compatible with and contains the vector which includes an inserted DNA gene sequence coding for human PRI, and a substantially pure recombinant human PRI protein having a molecular weight of about 51,000 daltons. The vector can comprise, for example, a plasmid DNA strand containing a foreign gene sequence coding for human PRI.

The invention further includes a recombinant host cell capable of expressing human PRI, comprising the host cell, a promoter, and a foreign gene sequence coding for human PRI which is subject to the control of the promoter.

In addition, in accordance with the invention, the gene sequence coding for recombinant human PRI has been determined.

Further objects, features and advantages of the invention will be apparent from the following detailed description of the invention and the illustrative drawings.

BRIEF DESCRIPTION OF THE DRAWINGS

FIGS. 3A, 3B, 3C illustrate the nucleotide sequence of the cloned gene coding for human PRI.

DETAILED DESCRIPTION OF THE INVENTION

Figure 1:
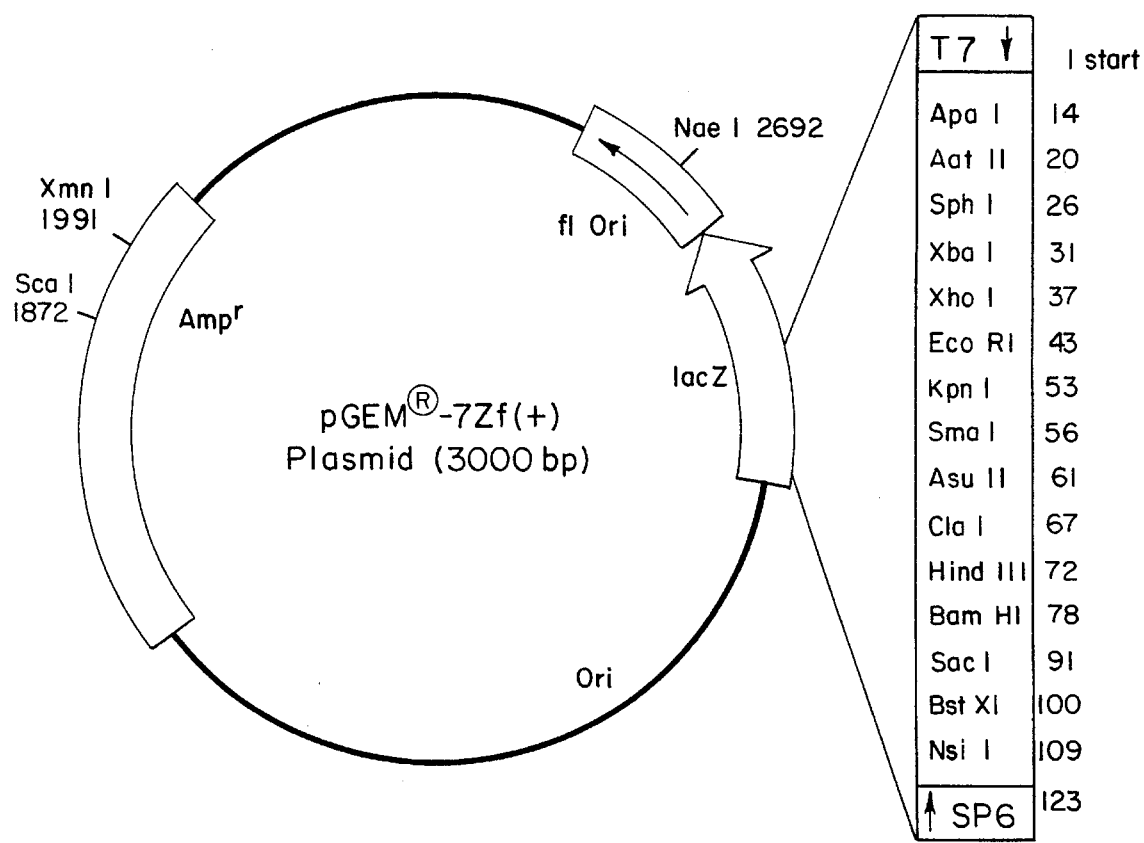
FIG. 1 is an illustration of a partial restriction site and functional map of the plasmid pGEM®-7Zf(+).

The present invention is directed to a method for obtaining a gene encoding for human PRI, expressing the product of this gene, and purifying and refolding the recombinant human PRI. The PRI may be obtained from a host cell which carries a plasmid containing the gene for the PRI protein. The DNA sequence of the gene for human PRI is also described.

An important aspect of the present invention involves the isolation of the inactive recombinant PRI, the solubilization of the recombinant PRI and the activation of the solubilized recombinant PRI.

A variety of vectors can be used to carry the gene coding for recombinant PRI into host cells. Vectors which may be used include a variety of plasmids such as pGEM®-7Zf(+), pBR322, PA3, pBC12B1 and pGPD-2 and derivatives thereof, and bacteriophage such as lambda gt11, $T_7$ and derivatives thereof.

Typical host cells include both prokaryotes such as E. coli and eukaryotes such as yeast. The host cell, in combination with the vector and the foreign gene sequence coding for PRI, which is subject to the control of the promoter, make up the recombinant host cell capable of expressing human PRI.

The recombinant PRI is characterized by a number of properties, among them:

a) molecular weight: 51,000 daltons b) type of inhibition: non-competitive

Additionally the recombinant PRI of the present invention is distinguished from PRI from a natural source by a number of characteristics. For example, unlike the PRI from a natural source, the N-terminal amino acid of the recombinant PRI is specified. Additionally and unlike the natural PRI, the recombinant PRI is not blocked and not acetylated. Further, the gene coding for recombinant PRI is free of mammalian DNA, prions and other potentially detrimental material such as, for example, HIV.

The inactive recombinant PRI is present as an inclusion body in a host cell. Typically, the inclusion body is a densely packed, granular protein mass. In order to isolate the PRI from the host cell, the cell membrane must be disrupted. Although there are several known cell lysis techniques available, the preferred method involves the use of an appropriate amount of lysozyme followed by centrifugation and a second treatment with sodium dodecyl sulfate (SDS). This process yields about 0.1% soluble active PRI in solution and about 99.9% insoluble, inactive PRI. The insoluble protein is removed in the form of crude, inactive protein by centrifugation. The protein is further purified by buffer suspension/centrifugation techniques.

After the inactive PRI protein has been isolated and purified, it is next solubilized, i.e., placed into solution. Solubilization is initiated in a buffer solution preferably containing a chemical agent intended to separate the polypeptide chains from each other in a solution. Examples of useful chemical agents include urea, guanidine HCl and SDS, with urea being the preferred chemical agent. Prior to use, the urea solution is preferably centrifuged to remove unwanted debris and cell matter. The solubilization step should take place over a relatively short span of time, i.e., no more than 30 minutes. It has been discovered that there is an inverse correlation between the length of time that the inactive PRI associates with the chemical agent and the final yield of active PRI.

The activation step involves the dilution of the solution containing the PRI in a buffer solution for a time sufficient to allow the PRI to refold to an active state. Several factors are important for the activation state. For example, the dilution step should take place relatively quickly, i.e., within 2 minutes, preferably within 30 seconds. The buffer solution should have a pH in the range of about 6.5 and about 8.5, preferably about 7.5. It is also helpful to provide the buffer solution with a water active agent such as glycerol and sucrose. It has been discovered that the presence of a sufficient quantity of water active agent in the buffer solution enhances the PRI protein refolding ability. It has also been found that a dilution rate of about 1 part PRI solution to about 100 parts buffer solution is optimal to assist in refolding the PRI.

After the solution has been diluted, it should be allowed to remain undisturbed for a period of time not less than 8 hours, and preferably between 8 and 18 hours at a temperature between about 10° C. and 25° C. Under these conditions, the PRI protein should refold such that about 7% of PRI molecules will become active.

The following examples are provided as illustrative of the methods for producing a cloned gene encoding for human PRI and for producing active recombinant human PRI.

Example 1

Isolation of a Lambda gt11 Clone Containing a Gene for Human PRI

Before the gene for human PRI can be cloned, a substantially pure natural human PRI protein must be obtained. The human PRI protein is prepared according to the process of Blackburn, et al. (.supra) which is incorporated herein by reference for a description of the purification process. Briefly, a soluble ribonuclease inhibitor from the human placenta can be purified 4,000 fold by a combination of ion exchange and affinity chromatography described in Blackburn, et al. (supra).

PRI protein from the natural source was purified to apparent homogeneity according to the method described in Blackburn, et al. (supra). The protein was further purified by binding to and eluting from DEAE Sepharose CL-6B by gradient elution, a process which removes a functional contaminant whose presence may not be obvious from gel analysis.

A laboratory animal, a New Zealand white rabbit, was immunized with 1 mg. of the purified PRI protein, followed by subsequent booster injections, and bled at 10 weeks. A commercial cDNA library (Clontech, Palo Alto, Calif.) of human placenta in the bacteriophage lambda gt11, was screened according to the procedure listed in the *Protoblot Immunoscreening Manual* (Promega Corporation, 1987), which is incorporated herein by reference. Briefly, the library was plated on *E. coli* Y1090 (r minus) at a density of 50,000 plaques per plate and 10 plates were screened for a total of 500,000 plaques. A plaque giving a strong positive signal was identified.

The plates were overlayered with nitrocellulose filter discs which had been soaked in isopropyl-beta-D-thiogalactopyranoside (IPTG). Following adsorption of the proteins to the filters, the filters were lifted and the rest of the protein binding sites on the filters were blocked by incubation in a buffer containing 1% v/v bovine serum albumin (BSA). The filters were then exposed to a 1,000 fold dilution of the rabbit antibody, diluted in buffer and shaken gently at room temperature for approximately 30 minutes. The filters were then washed 3 times in buffer and exposed to a 1:7500 dilution of commercially available goat anti-rabbit IgG alkaline phosphatase conjugate (Promega Corporation). This "second antibody" detects the presence of a first antibody bound to the PRI fusion protein on the filter. Following a 30 minute room temperature incubation in the presence of the second antibody, the filters were then washed 3 times in buffer. A substrate solution for alkaline phosphatase was then added and the color development allowed to proceed. One plaque giving a strong positive signal was observed in a single run of screening 500,000 plaques. The plaque producing the strong positive was then purified to homogeneity by cutting out tile plaque and replating until the particular phage was pure.

The DNA from the recombinant lambda phage carrying a putative PRI gene was purified using a commercially available phage absorbent (Lambdasorb®, Promega Corporation) by immunoprecipitation. Restriction analysis of the phage DNA indicated that a single 1.6 kilobase (kb) insert was present. This insert could be removed from the phage DNA by digestion with the enzyme Eco Rl. Since the PRI protein would require a 1.4 kb gene in order to encode for it, this insert was of an appropriate size to carry the entire PRI gene. In general, eukaryotic messenger RNA's are longer than just required to carry a protein coding sequence, being augmented by a 5' untranslated region and a 3' untranslated region, as well as a region carrying a poly A tract.

Example 2

Subcloning the Gene Containing the PRI Insert Into a Plasmid

In Example 1, the PRI gene was removed from the lambda gt11 on a single Eco Rl fragment. Therefore, it was decided to directly subclone the fragment into the plasmid pGEM®-7Zf(+) (Promega Corporation). Reference is made to FIG. 1 for an illustration of the plasmid pGEM®-7Zf(+). By subcloning the fragment into the pGEM®-7Zf(+) plasmid, expression of the correct reading frame of the insert could be obtained.

The reading frame at the Eco Rl site of the pGEM®-7Zf(+) plasmid is the same as the Eco Rl site of the bacteriophage lambda gt11. Thus, if the coding sequence of the cDNA is expressed in lambda gt11, it will also be expressed in the pGEM®-7Zf(+) plasmid.

When the fragment is inserted into the vector in correct orientation, the promoter on the plasmid, i.e., the lac promoter, drives the expression of the PRI insert. Attached to the PRI protein is a protein segment derived from the first few amino acids of beta-galactosidase, as well as extra amino acids coded by the multiple cloning region in the pGEM®-7Zf(+) plasmid vector and any 5' non-coding regions present in the insert before the ATG of the PRI protein.

Figure 2:
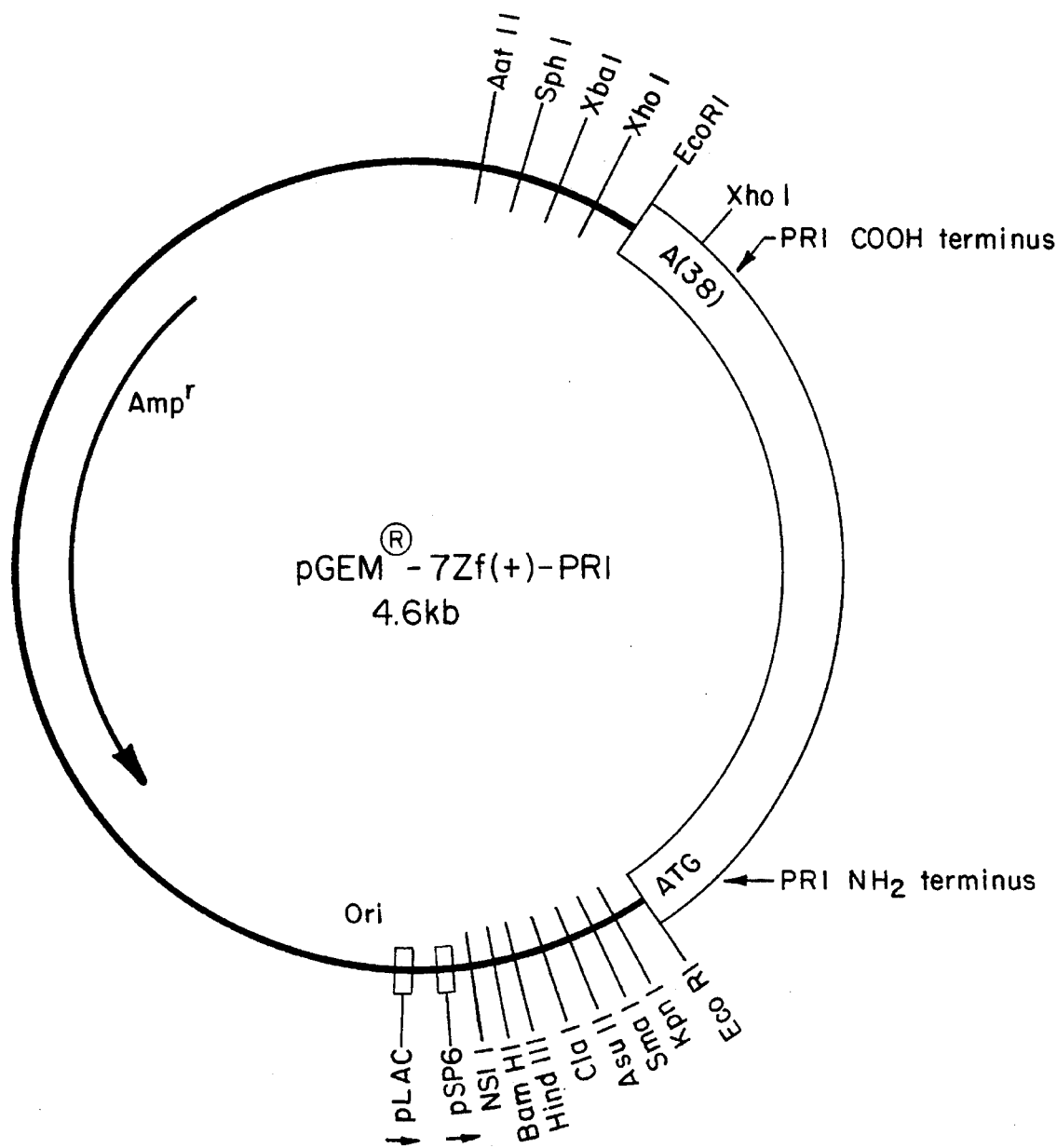
FIG. 2 is an illustration of a partial restriction site and functional map of the plasmid pGEM®-7Zf(+) having the gene sequence encoding for PRI inserted therein.

The bacteriophage lambda gt11 carrying the Eco Rl PRI insert was cut with Eco Rl and subcloned into the pGEM®-7Zf(+) plasmid by standard cloning techniques as described in Maniatis, et al., *Molecular Cloning. A Laboratory Manual,* (1982) Cold Spring Harbor, Laboratory Press, Cold Spring Harbor, N.Y. Reference is made to FIG. 2 for a map of this recombinant plasmid.

Example 3

Expression of PRI Insert in pGEM®-7Zf(+) Plasmid

When transferred into the pGEM®-7Zf(+) plasmid, the insert is in a frame for expression, i.e., the expression frame at the Eco Rl site in this plasmid is the same frame as the expression frame at the Eco Rl site in the lambda gt11. Therefore, the PRI fusion protein could be directly produced in *E. coli.* Following induction of expression by inducing the lac promoter on the pGEM®-7Zf(+) plasmid, a fusion protein with an apparent molecular weight of about 60,000 daltons was detected by Western blot analysis (Towbin, H., et al., *Proc. Natl. Acad. Sci. U.S.A.,* 76, 4350 (1979)) utilizing primary rabbit antibody against natural PRI as the probe.

It was expected that the fusion protein produced would be somewhat larger than the native PRI. This was, in fact, observed to be the case and is consistent with the hypothesis that the entire coding region of PRI was present on the Eco Rl insert.

Example 4

Production of PRI Protein in a Rabbit Reticulocyte Lysate

Following the cloning of the PRI insert into the pGEM®-7Zf(+) plasmid, the vector was now available for the synthesis of RNA from the insert in vitro using the SP6 promoter on the vector. RNA was synthesized from this promoter and used to program a rabbit reticulocyte lysate. A 51,000 dalton protein was synthesized which had the size of natural PRI protein. Again, this result indicates that the entire PRI coding sequence is contained on the clone.

Example 5

Sequencing of the Insert in the pGEM®-7Zf(+) Plasmid

An initial sequencing run of the 5' end and the 3' end of the PRI gene insert was performed on the clone in the pGEM®-7Zf(+) plasmid. The sequencing data indicated the presence of an ATG codon several nucleotides downstream from the Eco Rl cloning site and the presence of a poly A tail 36 residues in length at the 3' end of the cloned gene. From the size of the fusion protein produced according to Example 4, it was possible to conclude that the logical starting point for the PRI protein coding sequence was the first ATG codon discovered in the sequencing clone.

Further sequencing data was obtained by performing sequential exonuclease III deletions of the pGEM®-7Zf(+) clone using a commercial deletion system (Erase-a-Base® system, Promega Corporation). Exonuclease III was used to specifically digest DNA from a 5' protruding or blunt end, while leaving a 4-base 3' protruding end intact. The uniform rate of digestion of the enzyme allowed deletions to be made at predetermined intervals by removing timed aliquots from the reaction. The strategy eventually produced substantially the entire nucleotide sequence of the cloned insert. Reference is made to FIGS. 3–3C for an illustration of the nucleotide sequence of the cloned gene for human PRI obtained in this manner, which includes the derived amino acid sequence of the protein.

Given the nucleotide sequence of the cloned gene for human PRI, it would be within the scope of the present invention to construct a hybridization probe which would allow the isolation of the PRI gene by hybridization to a cDNA library.

Example 6

Engineering the Gene for Expression of the Natural Sequence Protein

To synthesize the natural sequence protein with no fusion partner attached to the gene product, it was assumed that the first ATG codon found in the sequencing on the clone was the natural translation start site. A prokaryotic ribosome binding site was then inserted 6 to 8 bases from the ATG start so that the start site would be functional in *E. coli.* From other constructions attempted, it appeared that PRI chimeric proteins with as few extra amino terminal amino acids as 8 were lethal when expressed from a regulatable *E. coli* promoter. It was therefore decided to drive the PRI gene with a T7 promoter, as described in Studier, F. William and Barbara A. Moffatt, "Use of Bacteriophage T7 RNA Polymerase to Direct Selective High-Level Expression of Cloned Genes," *J. Mol. Biol.,* 189, 113–130 (1986).

The constructions were then completed and propagated in an *E. coli* host devoid of T7 RNA polymerase. Thus, the gene could be kept silent until transferred into a host expressing the RNA polymerase. Such expression systems have been described (Studier, et al., supra, and Rosenberg, Alan H., et al., "Vectors for Selective Expression of Cloned DNA's by T7 RNA Polymerase," *Gene,* 56, 125–135 (1987)) and were essentially followed in this example.

In a preferred construction, the ribosome binding site and spacing before the ATG codon, as well as the 5' untranslated leader which follows before the Shine-Dalgarno sequence, derive from the bacteriophage T7 gene 10 leader and ribosome binding site. In addition, a T7 promoter is present in order to drive production of this RNA.

The transfer of the PRI gene from lambda gt11 into the pGEM®-7Zf(+) plasmid opened up a variety of cloning strategies due to the fact that the gene was now flanked by multiple cloning restriction enzyme sites present in the plasmid.

The PRI gene was excised on a Bam Hl-Aat II fragment and placed into a plasmid vector pBR322 between these two sites. A T7 terminator of the sequence referred to in Rosenberg, et al. (supra) and synthesized as a synthetic oligonucleotide, was then inserted after the gene between the Xba I and Aat II sites. The Xba I site was derived from the pGEM®-7ZF(+) linker upon transfer of the PRI gene on the Bam Hl-Aat II fragment.

A synthetic oligonucleotide was synthesized that carried the T7 promoter and the gene 10 5' untranslated sequence and the gene 10 Shine-Dalgarno sequence.

The nucleotide was inserted into the beginning of the PRI gene between the Bam HI and the BstXI sites of the clone. The sequence analysis of the beginning of the PRI insert revealed a BstXI site after the third codon of the presumptive gene sequence. The oligonucleotide was designed to replace those amino acids since BstXI cuts just into the coding sequence. The final construct is illustrated in FIG. 4 and constitutes the PRI gene in the plasmid pBR322 engineered for expression in *E. coli*.

Figure 4:
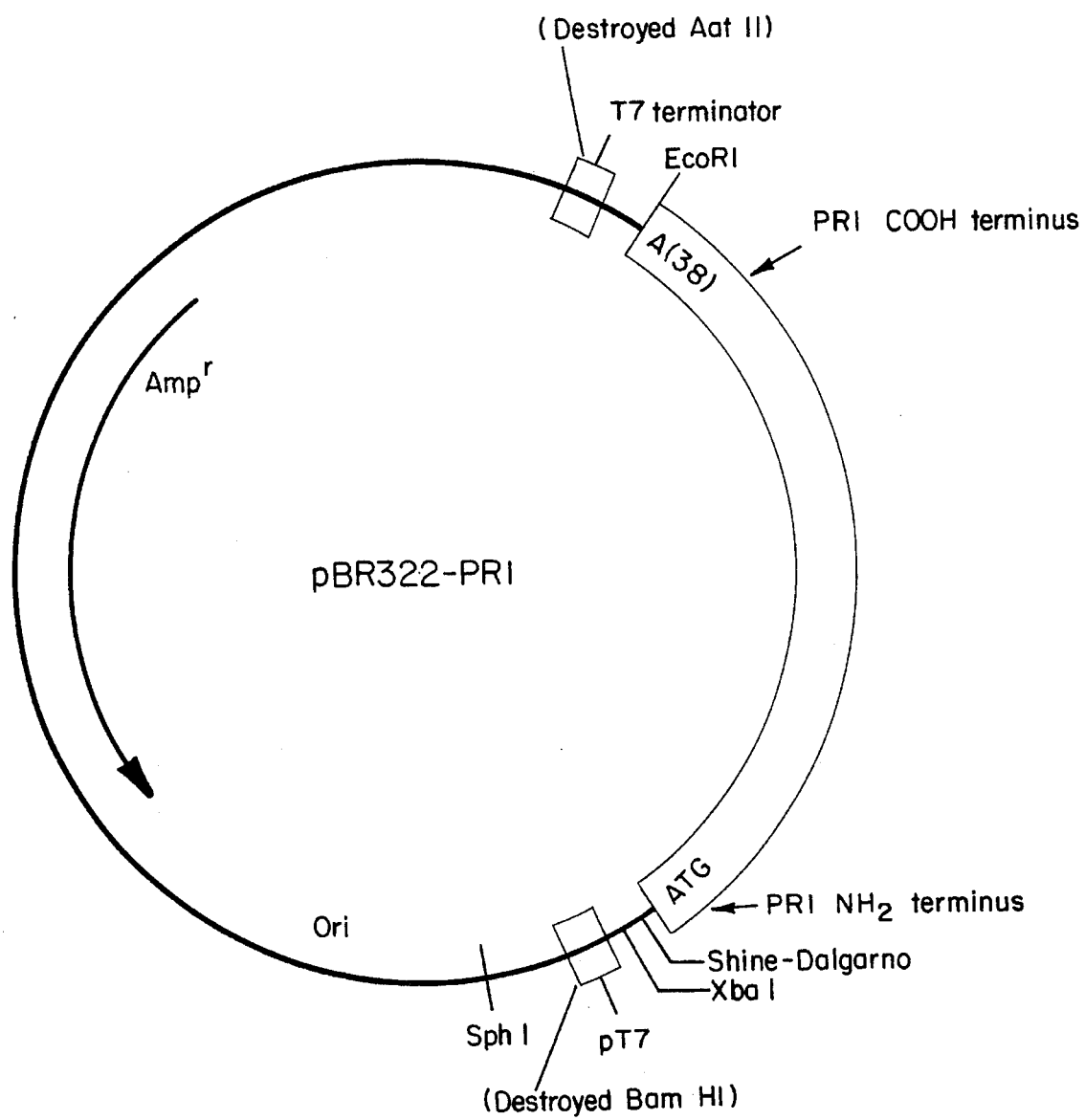
FIG. 4 is an illustration of a partial restriction site and function map of a pBR322 plasmid having the gene sequence encoding for PRI inserted therein and engineered for expression.

To express the PRI gene in this synthetic construct, the plasmid diagrammed in FIG. 4 was placed into an *E. coli* strain which produces T7 RNA polymerase. The strain was constructed according to the methods described in Studier, et al. (supra) and Rosenburg, et al. (supra). An *E. coli* strain JM 109 was lysogenized with wild type phage lambda. This strain was used as a host for infection by a recombinant lambda phage (lambda D69-T7) carrying the gene for T7 RNA polymerase inserted into the Bam HI site of the lambda vector. The gene for the T7 RNA polymerase was inserted into the chromosome of the *E. coli* strain JM109-DE3. A deposit of the clone was made with the American Type Culture Collection, 12301 Parklawn Drive, Rockville, Md. 20850, on Feb. 21, 1990 and received accession number 68230.

A culture was grown to an optical density of 1 and induced with IPTG. The PRI protein which was produced was monitored by polyacrylamide gel electrophoresis (PAGE) (Laemmli, U.K., *Nature* (London), 227, 680 (1970) of the bacteria proteins followed by Western blotting (Towbin, H., et al., supra.) and detection using primary rabbit antibody against PRI protein. The analysis indicated that following induction of the PRI culture with IPTG and growth for 4 hours, about 40 mgs. of PRI was synthesized per liter of culture.

Example 7

Production of Active PRI in *E. coli* JM 109

*E. coli* JM 109-DE3, carrying the PRI plasmid described in Example 6, can produce a certain level of active PRI protein. Although most of the protein is synthesized in an inactive and insoluble form, about 0.1% of the total PRI protein is both soluble and active. The active PRI protein may be purified from centrifuged French pressed lysates (Scopes, Robert K., *Protein Purification-Principles and Practice*, 2nd ed., 27, 1987) of this strain using batch absorption onto an affinity matrix containing bound RNase. The PRI recovered by this procedure has the same molecular weight on gels as natural PRI, a non-glycosylated protein described in Blackburn, et al. (supra) and Blackburn (supra), and about the same specific activity as the purified natural product.

Because most of the PRI protein produced in *E. coli* was synthesized in an insoluble form, to obtain an economical way of producing the active recombinant PRI protein, the insoluble material first had to be solubilized and refolded into an active form.

Example 8

Production of PRI Protein Under the Control of the *E. coli* Tac Promoter

The natural PRI protein was also produced in *E. coli* under the control of the strong host promoter pTac in a pTTQ vector (Stark, J.J.R., *Gene*, 51, pp. 255–267, 1987).

The PRI insert was removed from pBR322 on an Sph I-Eco Rl fragment, which contains the good ribosome binding site and precedes the PRI gene, and cloned into the vector pTTQ19 (Amersham) between the SphI and Eco Rl sites. This construction enabled the PRI gene to be driven by the Tac promoter on a bicistronic message. One ribosome binding site is contributed by the pTTQ vector and the other by the PRI insert. Because internal ribosome binding sites function well in *E. coli*, the natural PRI protein, not a fusion protein, will be synthesized in this construct. The construct was placed into several different *E. coli* hosts in order to see which host gave the best levels of soluble and active protein. The hosts tested included *E. coli* C6000, JM109, NM522, BSJ 72, B121 and HB101. At least some soluble and active PRI was produced in each of the hosts tested.

Example 9

Secretion of PRI Protein in *E. coli*

The PRI protein might have a number of disulphide linkages as the amino acid analysis of the natural protein indicates 32 cysteines per molecule. These bonds might not form correctly in the reducing environment of the cytoplasm. Therefore, it was decided to attempt to secrete the protein into the bacterial periplasmic space where under more oxidizing conditions correct disulphide bond formation might take place. pBR322-PRI was modified by the addition of a synthetic oligonucleotide coding for the signal sequence of the *E. coli* ompA protein (Movva, N.R., et al., *J. Mol. Biol.*, 143, pp. 317–238, 1980) placed before the start of the PRI gene. These leader amino acids target a protein for secretion and are cleaved off by the *E. coli* signal peptidase during secretion of the protein from the cell. In this construct the T7 promoter continues to drive transcription of the PRI gene, as in pBR322-PRI, but the ompA signal sequence is made first. Results indicated that PRI was correctly processed (the signal sequence removed) and secreted from the cell. The secreted PRI protein was found not to be active. Furthermore, levels of protein were about 10 fold lower than that produced inside the cell, amounting to only about 4 mg per liter of culture.

Example 10

Examples of PRI Constructs that are Lethal to *E. coli*

During the course of the construction of a useful expression vector for human recombinant PRI, several situations were encountered in which the expression of the PRI protein was not possible because these constructs proved to be lethal to the host cell. One such case was the attempted construction of a PRI fusion with twelve extra amino terminal amino acids in the vector pTTQ9, and another the secretion of PRI in the secretion expression vector PINIIIompA (Masui, Y., et al., "Multipurpose Expression Cloning Vehicles in *Escherichia coli*," *Experimental Manipulation of Gene Expression*, M. Inouye, Ed., Academic Press, 1983). In the first case, the Pst I site of pTTQ9 was first cut with Pst I, the ends blunted with Klenow, and the vector religated. The PRI insert from pGEM®-7Zf(+)-PRI was then removed on a Bam Hl-Sph I fragment and cloned between the Bam HI and Eco Rl sites of the Pst I filled pTTQ9 vector. Cutting then with Sal I and Kpn I followed by Klenow treatment of these sticky ends and religation would have put the PRI gene in frame for fusion protein expression from the strong Tac promoter on the vector. Since it was not possible to obtain the final constuct, it was concluded that this expression system cause lethal amounts of PRI fusion protein to be produced, even under uninduced conditions. It was later determined that this same fusion protein could be produced under the control of a T7 promoter, in essentially the same construct as pBR322-PRI, but this time with the clone engineered at the amino terminus to incorporate the extra twelve amino acids. The difference in the ability to produce the fusion protein in one expression system but not in the other is perhaps due to the greater repression of the T7 system under conditions of non-induction.

In the attempt to clone the PRI insert into the secretion vector pIN IIIompA, lethality was also observed. The PRI insert was excised from pGEM®-7Zf(+)-PRI on the BstXl-EcoRl fragment and cloned into EcoRl cut phosphatased pIN IIIompA. The PRI fragment could be inserted in two different orientations, directed so that the PRI gene is forwards or backwards with respect to the Tac promoter on the vector. The only observed constructs, however, were those in which the PRI insert was oriented backwards with respect to this promoter, and thus no expression of the gene was obtained. The forwards construct appears to be lethal, for reasons alluded to above.

Example 11

Isolation and Recovery of Insoluble PRI Produced in *E. coli*

The insoluble PRI produced in *E. coli* cells induced for production of this protein can be recovered as follows:

1. The cells induced for the production of the inactive PRI are suspended in a buffer solution. A suitable buffer solution is TE5DTT buffer including 50 mM Tris-HCl (pH 7.5), 5 mM EDTA and 5 mM DTT. A suitable suspension includes approximately 20 grams of the cells, generally in a frozen state, in 400 ml. of the buffer solution. It is within the scope of this invention to scale the process up or down. However, it is preferred that a 1:20 ratio (gram cells/ml. buffer) be maintained.

2. The suspension is stirred vigorously for approximately 10 minutes on ice.

3. The cell membranes are then disrupted by cell lysis. A preferred cell lysis method includes adding powdered lysozyme (SIGMA grade VI) at a concentration of 1 mg/ml followed by stirring for 30 minutes on ice. After stirring, approximately 4 ml of 10% (v/v) sodium dodecyl sulfate (SDS) is added, again followed by 30 minutes of stirring on ice.

4. The suspension is then centrifuged at, preferably, about 17,000×g for approximately 20 minutes at a temperature of about 4° C. A biphasic pellet will be recovered consisting of a greyish hard lower layer, a translucent slimy layer and supernatant.

5. The supernatant is decanted from the pellet carefully leaving the pellet intact. The pellet is the crude PRI protein.

Example 12

Purification of PRI

1. The crude PRI is isolated by resuspending the pellet obtained as in Example 11 in a buffer under similar conditions as in Example 11.

2. The suspension is then recentrifuged at approximately 17,000×g for approximately 20 minutes at a temperature of about 4° C. After centrifugation, much less of the slimy layer will be present.

3. The supernatant is then decanted from the centrifuged mixture.

4. The pellet is resuspended in a buffer solution with stirring. Preferably, the buffer solution is TE5DTT in an amount of 400 ml. per 20 grams of pellet. The suspension is stirred vigorously for approximately 30 minutes on ice.

5. The suspension is then recentrifuged at preferably 17,000×g for about 20 minutes at a temperature of about 4° C. The remaining pellet will be slightly grey in color.

Example 13

Solubilization of PRI

The pellet is resuspended and solubilized in the following manner:

1. The final pellet is resuspended in a buffer solution, preferably 200 ml. TE5DTT, with stirring for approximately 120 minutes on ice. A white milky suspension will result.

2. Solubilization is initiated in a buffer solution preferably containing urea in a concentration no less than 4M. A suitable buffer solution is TE5DTT. The urea solution preferably includes 800 ml. TE5DTT containing 360 g. urea.

3. The solubilized PRI is diluted at a rate of approximately 200 ml. PRI to 800 ml. buffer solution at a temperature between about 10° C. and 25° C. with rapid stirring. After the solution has been stirred for about 3 to 5 minutes, the solution should become almost clear with some debris.

4. Prior to use, the urea solution is preferably centrifuged to remove undissolved material. Centrifugation is accomplished at 6,000×g for approximately 15 minutes at a temperature of about 4° C. A supernatant results, which is clear and colorless. The supernatant contains the solubilized PRI.

Example 14

Activation of PRI

The supernatant is rapidly diluted into 100 L of a buffer solution for a time sufficient to allow the PRI to refold to an active state. Preferably, the buffer solution is TE5DTT including 10% (v/v) of a water active agent. A preferred water active agent is glycerol, although sucrose may be substituted. The buffer solution has a pH between about 6.5 and about 8.5, preferably 7.5.

After the solution has allowed to sit for approximately 8 to 18 hours at room temperature, the PRI protein will have refolded such that about 7% of the molecules will become active.

Example 15

Separation of Refolded and Inactive PRI

The refolded PRI in the 100 L volume can be concentrated on a diethyl amino ethyl (DEAE) column reactor. The DEAE column is advantageous in that in that it not only concentrates the refolded PRI but also has been found to assist in completing the refolding process of the PRI protein, which is of significant advantage to the present invention. An exemplary column is a Curio® 3200 DEAE cartridge at a flow rate of 30 liters/hour. The procedure is as follows:

1. The refolded PRI is pumped onto the cartridge and eluted with TE5DTT which also contains 0.5 M NaCl.

2. The eluate from the column is then applied to an affinity resin containing at least 1 mg/ml covalently bound RNase. The active PRI sticks to the RNase column while the inactive improperly folded material flows through in the affinity column fraction.

3. The active PRI is eluted from the affinity resin with 0.05 M Na-acetate buffer, pH 5.0+3M NaCl also containing 5 mM DTT. At this stage, the PRI is essentially pure and is homogeneous by PAGE.

4. If RNase contamination is a problem, the PRI protein may be further cleaned away from functional impurities by binding to and gradient elution from a DEAE Sepharose CL-6B. The yield of PRI from 20 grams of cells by refolding and purification steps is about three million units.

The recombinant protein can be distinguished from the natural protein by the presence of an unblocked amino terminus on the recombinant protein. We have found that the natural source PRI cannot be sequenced from its amino end because its amino terminus is blocked, presumably by acetylation. Protein sequencing of the recombinant protein demonstrates an unblocked amino terminus for the recombinant, and furthermore indicates that the N terminal methionine has been removed in *E. coli*.

It is understood that the invention is not limited to the particular embodiments specifically disclosed herein as exemplary, but embraces such modified forms thereof as come within the scope of the following claims.

What is claimed is:

1. A method of solubilizing and refolding into active form human placental ribonuclease inhibitor from insoluble inclusion bodies formed in *E. coli* cells by expression therein of a cDNA encoding said inhibitor, comprising:
   a) isolating the insoluble, inactive human placental ribonuclease inhibitor from said cells;
   b) solubilizing the inactive human placental ribonuclease inhibitor of step a) wherein the solubilization process comprises combining the insoluble, inactive human placental ribonuclease inhibitor with a buffer solution comprising urea in a concentration no less than about 4 M; and
   c) activating the human ribonuclease inhibitor by dilution thereof.

2. The method of claim 1 wherein the isolation process of step a) comprises;
   a) suspending cells induced for the production of the inactive human placental ribonuclease inhibitor in a buffer solution;
   b) disrupting the cell membranes of the cells by cell lysis;
   c) centrifuging a human placental ribonuclease inhibitor pellet from the solution of step b); and
   d) decanting the supernatant from the centrifuged human placental ribonuclease inhibitor pellet.

3. The method of claim 2 wherein a sufficient amount of lysozyme and SDS are added to the suspension of step a) to disrupt the cell membrane, and centrifugation is performed at about 17,000×g at a temperature of about 4° C.

4. The method of claim 1 wherein the buffer contains 50 mM Tris-HCl, 5 mM EDTA and 0.5 mM DTT and has a pH of about 7.5.

5. The method of claim 1 further comprising centrifuging the solubilized human placental ribonuclease inhibitor solution to remove undissolved material.

6. The method of claim 1 wherein the activation process of step c) comprises diluting the solubilized human placental ribonuclease inhibitor in a buffer solution for a time sufficient to allow the human placental ribonuclease inhibitor to refold to an active state.

7. The method of claim 6 wherein the buffer solution contains 50 mM Tris-HCl, 5 mM EDTA and 0.5 mM DTT and has a pH of about 7.5.

8. The method of claim 6 wherein dilution is at a ratio of at least 20 parts buffer to 1 part urea-containing solution comprising solubilized human placental ribonuclease inhibitor.

9. The method of claim 6 wherein the solubilized human placental ribonuclease inhibitor is diluted at a temperature of between about 10° C. and 25° C.

10. The method of claim 6 wherein the buffer solution has a pH between about 6.5 and about 8.5, and wherein the buffer solution further contains DTT in a concentration not less than 0.5 mM.

11. The method of claim 6 wherein the buffer solution contains a water active agent selected from the group consisting of sucrose and glycerol.

12. A method of solubilizing an inactive form of human placental ribonuclease inhibitor from an insoluble inclusion body formed in *E. coli* cells by expression therein of a cDNA encoding said inhibitor, comprising:
   a) isolating the inactive human placental ribonuclease inhibitor from the *E. coli* cells; and
   b) combining the inactive human placental ribonuclease inhibitor with a buffer solution comprising urea in a concentration no less than about 4 M.

13. The method of claim 12 wherein the buffer contains 50 mM Tris-HCl, 5 mM EDTA and 0.5 mM DTT and has a pH of about 7.5.

* * * * *

UNITED STATES PATENT AND TRADEMARK OFFICE
CERTIFICATE OF CORRECTION

PATENT NO.  : 5,552,302
DATED       : September 3, 1996
INVENTOR(S) : Martin K. Lewis, et al.

It is certified that error appears in the above-indentified patent and that said Letters Patent is hereby corrected as shown below:

In column 1, line 23 of the patent, --DNA-- should be inserted before "sequences".

In column 2, line 66 of the patent, "vallee" should be --Vallee--.

In column 3, line 23 of the patent, "tile" should be --the--.

In column 5, line 48 of the patent, "(.supra)" should be --(supra)--.

In column 5, line 55 of the patent, "tile" should be --the--.

In column 6, line 28 of the patent, "tile" should be --the--.

In column 12, line 66 of the patent, "Curio®" should be --Cuno®--.

Signed and Sealed this

Eighth Day of April, 1997

Attest:

BRUCE LEHMAN

*Attesting Officer*     *Commissioner of Patents and Trademarks*